US006624187B1

United States Patent
Pandey et al.

(10) Patent No.: US 6,624,187 B1
(45) Date of Patent: Sep. 23, 2003

(54) LONG WAVE LENGTH ABSORBING BACTERIOCHLORIN ALKYL ETHER ANALOGS

(75) Inventors: Ravindra K. Pandey, Williamsville, NY (US); Thomas J. Dougherty, Grand Island, NY (US); William R. Potter, Grand Island, NY (US)

(73) Assignee: Health Research, Inc., Buffalo, NY (US)

( * ) Notice: Subject to any disclaimer, the term of this patent is extended or adjusted under 35 U.S.C. 154(b) by 0 days.

(21) Appl. No.: 09/592,150

(22) Filed: Jun. 12, 2000

(51) Int. Cl.[7] .................... C07D 487/22; A61K 31/40

(52) U.S. Cl. .................... 514/410; 540/471; 540/472; 540/145; 514/185; 424/9.6

(58) Field of Search .................... 540/471, 472, 540/145; 424/9.6; 600/431; 514/410, 185

(56) References Cited

U.S. PATENT DOCUMENTS

| | | | |
|---|---|---|---|
| 4,649,151 A | 3/1987 | Dougherty et al. | 514/410 |
| 4,753,958 A | 6/1988 | Weinstein et al. | 514/410 |
| 4,866,168 A | 9/1989 | Dougherty et al. | 540/145 |
| 4,889,129 A | 12/1989 | Dougherty et al. | 128/664 |
| 4,932,934 A | 6/1990 | Dougherty et al. | 604/21 |
| 4,968,715 A | 11/1990 | Dougherty et al. | 514/410 |
| 5,002,962 A | 3/1991 | Pandey et al. | 514/410 |
| 5,015,463 A | 5/1991 | Dougherty et al. | 424/7.1 |
| 5,028,621 A | 7/1991 | Dougherty et al. | 514/410 |
| 5,062,431 A | 11/1991 | Potter | 128/665 |
| 5,074,632 A | 12/1991 | Potter | 385/31 |
| 5,093,349 A | 3/1992 | Pandey et al. | 514/410 |
| 5,145,863 A | 9/1992 | Dougherty et al. | 514/410 |
| 5,173,504 A | 12/1992 | Dougherty | 514/410 |
| 5,190,966 A | 3/1993 | Dougherty et al. | 514/410 |
| 5,198,460 A | 3/1993 | Pandey et al. | 514/410 |
| 5,225,433 A | 7/1993 | Dougherty et al. | 514/410 |
| 5,257,970 A | 11/1993 | Dougherty | 604/20 |
| 5,314,905 A | 5/1994 | Pandey et al. | 514/410 |
| 5,403,308 A | 4/1995 | Wood et al. | 606/17 |
| 5,459,159 A | 10/1995 | Pandey et al. | 514/410 |
| 5,498,710 A | 3/1996 | Pandey et al. | 540/145 |
| 5,506,255 A | 4/1996 | Smith et al. | 514/410 |
| 5,576,013 A | 11/1996 | Williams et al. | 424/423 |
| 5,591,847 A | 1/1997 | Pandey et al. | 540/472 |
| 5,591,855 A | 1/1997 | Hudkins et al. | 546/256 |
| 5,671,317 A | 9/1997 | Weishaupt et al. | 385/137 |
| 5,770,730 A | 6/1998 | Pandey et al. | 540/472 |
| 5,824,657 A | 10/1998 | Hill et al. | 514/46 |
| 5,849,692 A * | 12/1998 | Jonczyk et al. | 514/11 |
| 5,864,035 A | 1/1999 | Pandey et al. | 540/472 |
| 5,952,329 A | 9/1999 | Cincotta et al. | 514/224.5 |
| 5,952,366 A | 9/1999 | Pandey et al. | 514/410 |
| 5,981,492 A * | 11/1999 | Zoller et al. | 514/20 |
| 6,071,944 A | 6/2000 | Rodgers et al. | 514/408 |
| 6,103,751 A | 8/2000 | Pandey et al. | 514/410 |
| 6,107,480 A | 8/2000 | Funken et al. | 540/145 |
| 6,534,040 B2 | 3/2003 | Pandey et al. | 424/9.362 |

FOREIGN PATENT DOCUMENTS

| | | |
|---|---|---|
| EP | 0161606 A2 | 11/1985 |
| EP | 0161606 A3 | 11/1985 |
| EP | 0276121 A2 | 7/1988 |

(List continued on next page.)

OTHER PUBLICATIONS

Zheng et al. Bioorg. Med. Chem. Lett. 10 (2000) 123–127.*
Roberts et al. J. Natl. Cancer Ins. 80: 330–336 (1998).*
Taber's Cyclopedic Medical Dictionary, 14th edition (1981), p. 63.*

(List continued on next page.)

Primary Examiner—Richard L. Raymond
Assistant Examiner—Kahsay Habte
(74) Attorney, Agent, or Firm—Heller Ehrman White & McAuliffe LLP; Stephanie L. Seidman

(57) ABSTRACT

Novel compounds that either preferentially absorb into hyperproliferative tissue and absorb light efficiently at a wavelength of between about 700 and about 850 nm or act as intermediates for such absorbing compounds. More particularly, the compounds of the invention have the formula:

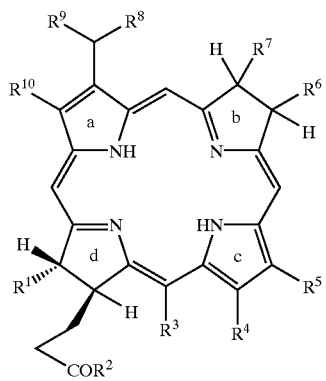

where $R^1$, $R^5$, $R^9$, and $R^{10}$ are independently lower alkyl of 1 to 3 carbon atoms provided that at least three of $R^1$, $R^5$, $R^9$, and $R^{10}$ are methyl; $R^2$ is —OH, —$OR^{11}$, —$NHR^{11}$, aryl, or -aminoacid; $R^3$ and $R^4$ are independently —$COR^{11}$ or taken together are

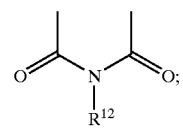

$R^6$ and $R^7$ are independently lower alkyl of 1 to 3 carbon atoms; $R^8$ is O-alkyl of 1 to about 12 carbon atoms, S-alkyl of 1 to about 12 carbon atoms, —O-aryl, or —O-heterocyclic ring of 5 or 6 carbon atoms; $R^{11}$ is alkyl of 1 to 6 carbon atoms; and $R^{12}$ is lower alkyl of 1 to about 12 carbon atoms, aryl, or aminoalkyl of 1 to 8 carbon atoms; provided that at least one of $R^8$, $R^{11}$, and $R^{12}$ is hydrophobic and together contain at least 10 carbon atoms. The invention also includes method of making and using the compounds.

18 Claims, 5 Drawing Sheets

FOREIGN PATENT DOCUMENTS

| | | | |
|---|---|---|---|
| EP | 0120054 | B1 | 5/1990 |
| EP | 0161606 | B1 | 4/1993 |
| EP | 0423195 | B1 | 4/1994 |
| EP | 0425566 | B1 | 10/1994 |
| EP | 0450149 | B1 | 5/1996 |
| EP | 0468997 | B1 | 3/1997 |
| EP | 0891977 | A1 | 1/1999 |
| EP | 0682956 | B1 | 2/2000 |
| EP | 1110963 | A2 | 6/2001 |
| EP | 1146046 | A2 | 10/2001 |
| EP | 1164136 | A1 | 12/2001 |
| EP | 1256586 | A1 | 11/2002 |
| JP | 6105921 | | 4/1994 |
| JP | 2001335578 | | 12/2001 |
| JP | 2002020389 | | 1/2002 |
| WO | 8401382 | | 4/1984 |
| WO | 0220686 | | 6/1987 |
| WO | 9000392 | | 1/1990 |
| WO | 9000895 | | 2/1990 |
| WO | 9012573 | | 11/1990 |
| WO | 9110474 | | 7/1991 |
| WO | 9313769 | | 7/1993 |
| WO | 9408631 | | 4/1994 |
| WO | 9532206 | | 11/1995 |
| WO | 9617844 | | 6/1996 |
| WO | 9631451 | | 10/1996 |
| WO | 9732885 | | 9/1997 |
| WO | 9959641 | | 11/1999 |
| WO | 9960191 | | 11/1999 |
| WO | 9967248 | | 12/1999 |
| WO | 9967249 | | 12/1999 |
| WO | 0061585 | | 1/2000 |
| WO | 0057199 | | 9/2000 |
| WO | 0061584 | | 10/2000 |

OTHER PUBLICATIONS

Robert and Caserio, Basic Principles of Organic Chemistry, 1965, p. 967.*

Morrison & Boyd, Organic Chemistry.*

USPTO Database Patent Search–"amino acid radical".*

Bellnier et al., "Design and construction of a light–delivery system for photodynamic therapy", *Med. Phys.,* 26(8):1552–1558 (1999).

Bellnier et al., "Distribution and Elimination of Photofrin II in Mice", *Photochem. Photobiol.,* 50(2):221–228 (1989).

Bellnier et al., "Protection of murine foot tissue and transplantable tumor against Photofrin–II–mediated photodynamic sensitization with WR–2721", *J. Photochem. Photobiol. B: Biol.,* 4:219–225 (1989).

Bellnier et al., "The Time Course of Cutaneous Prophyrin Photosensitization in the Murine Ear", *Photochem. Photobiol.,* 49(3):369–372 (1989).

Bernstein et al., "Photofrin photodynamic therapy for treatment of AIDS–related cutaneous Kaposi's sarcoma", *AIDS,* 13:1697–1704 (1999).

Boyle et al., "Photobleaching of Photofrin II as a Means of Eliminating Skin Photosensitivity", *Photochem. Photobiol.,* 46(6):997–1001 (1987).

Brasseur et al., "Photodynamic Activities and Skin Photosensitivity of the bis(Dimethylthexylsiloxy)Silicon 2,3–Naphthalocyanine in Mice", *Photochem. Photobiol.,* 62(6):1058–1065 (1995).

Dimitroff et al., "Anti–angiogenic activity of selected receptor tyrosine kinase inhibitors, PD166285 and PD173074; Implications for combination treatment with photodynamic therapy", *Investigational New Drugs,* 17:121–135 (1999).

Dougherty et al., "A Brief History of Clinical Photodynamic Therapy Development at Roswell Park Cancer Institute", *J. Clin. Laser Med. Surg.,* 14(5):219–221 (1996).

Dougherty et al., "Characterization of Intra–Tumoral Porphyrin Following Injection of Hematoporphyrin Derivative or Its Purified Component", *Photochem. Photobiol.,* 46(1):67–70 (1987).

Dougherty et al., "Energetics and Efficiency of Photoinactivation of Murine Tumor Cells Containing Hematoporphyrin", *Cancer Res.,* 36:2330–2333 (1976).

Dougherty et al., "Of what value is a highly absorbing photosensitizer in PDT?", *J. Photochem. Photobiol. B* 8(2): 223–225 (1991).

Dougherty, T.J., "Photodynamic Therapy", *Adv. Exp. Med. Biol.* 193: 313–28 (1995).

Dougherty, T.J., "Photodynamic Therapy (PDT) of Malignant Tumors", *Critical Reviews in Oncology/Hematology* 2(2):83–116 (1984).

Dougherty et al., "Photodynamic Therapy for Early Stage Lung Cancer", *Chest,* 102(5):1314–1315 (1992).

Dougherty, T.J., "Photodynamic Therapy", *Clinics in Chest Medicine,* 6(2):219–236 (1985).

Dougherty, T.J., "Photodynamic Therapy in Gastrointestinal Cancer" *Lasers Surg. Med.,* 12:114 (1992).

Dougherty et al., "Photoradiation Therapy. II. Cure of Animal Tumors With Hematoporphyrin and Light", *J. Natl'l. Cancer Institute,* 55(1):115–121 (1975).

Dougherty, T.J., "Photodynamic Therapy—New Approaches", *Seminars Surg. Oncol.,* 5:6–16 (1989).

Dougherty et al., "Photodynamic Therapy", *Photochem. Photobiol.,* 58(6):895–900 (1993).

Dougherty, T.J., "Photodynamic Therapy:: Part II", *Seminars Surg. Oncol.,* 11:333–334 (1995).

Dougherty, et al., "Photodynamic Therapy", *J. Nat'l. Cancer Institute,* 90(12):889–905 (1998).

Dougherty et al., "Photosensitizers: Therapy and Detection of Malignant Tumors", *Photochem. Photobiol.,* 45(6):879–889 (1987).

Dougherty et al., "The Structure of the Active Component of Hematoporphyrin Derivative", *Prog. Clin. Biol. Res.,* 170:301–314 (1984).

Henderson et al., "Bacteriochlorophyll–a as photosensitizer for photodynamic treatment of transplantable murine tumors", *J. Photochem. Photobiol. B: Biol.,* 10:303–313 (1991).

Ho et al., "Carbon–14 Labeling and Biological Activity of the Tumor–Localizing Derivative of Hematoporphyrin", *Photochem. Photobiol.* 48(4):445–449 (1988).

Ho et al., "Some Components of the Tumor–Localizing Fraction of Hematoporphyrin Derivative", *Photochem. Photobiol.,* 52(6):1085–1088 (1990).

Kessel et al., "Photosensitization of Diporphyrins Joined Via Methylene Bridges", *Photochem. Photobiol.,* 8(6):741–744 (1988).

Kessel et al., "Photosensitization of Synthetic Diporphyrins and Dichlorins in vivo and in vitro", *Photochem. Photobiol.,* 53(4):475–479 (1991).

Kessel et al., "Photosensitization with Bacteriochlorins", *Photochem. Photobiol.,* 58(2):200–203 (1993).

Khan et al., "An Evaluation of Photodynamic Therapy in the Management of Cutaneous Metastases of Breast Cancer", *Eur. J. Cancer,* 29A(12):1686–1690 (1993).

Kozyrev et al., "Thermolysis of vic–Dihydroxybacteriochlorins: A New Approach for the Synthesis of Chlorin—Chlorin and Chlorin_Porphyrin Dimers", *Org. Letts.*, 1(8):1193–1196 (1999).

Kripke et al., "Antigenicity of Murine Skin Tumors Induced by Ultraviolet Light", *J. Nat'l. Cancer Institute*, 53(5):1333–1336 (1974).

Lele et al., "Photodynamic Therapy in Gynecologic Malignancies", *Gynecologic Oncol.*, 34:350–352 (1989).

Li et al., "A Simple and Efficient Approach for the Synthesis of Fluorinated and Nonfluorinated Octaethylporphyin–Based Benzochlorins with Variable Lipophilicity, Their in Vivo Tumor Uptake, and the Preliminary in Vitro Photosensitizing Efficacy", *J. Org. Chem.*, 66:1316–1325 (2001).

MacDonald et al., "Subcellular Localization Patterns and Their Relationship to Photodynamic Activity of Pyropheophorbide–a Derivatives", *Photochem. Photobiol.*, 70(5):789–797 (1999).

Mang et al., "Photobleaching of Porphyrins Used in Photodynamic Therapy and Implications for Therapy", *Photochem. Photobiol.*, 45(4):501–506 (1987).

Mettath et al., "DNA Interaction and Photocleavage Properties of Porphyrins Containing Cationic Substituents at the Peripheral Position", *Bioconjugate Chem.*, 10:94–102 (1999).

Mettath et al., "Effect of Substituents in Directing the Formation of Benzochlorins and Isobacteriochlorins in Porphyrin and Chlorin Systems", *Org. Letts.*, 1(12):1961–1964 (1999).

Moesta et al., "Protoporphyrin IX Occurs Naturally in Colorectal Cancers and Their Metastases", *Cancer Res.*, 61:991–999 (2001).

Morgan et al., "Comparison of Photodynamic Targets in a Carcinoma Cell Line and Its Mitochondrial DNA–Deficient Derivative", *Photochem. Photobiol.*, 71(6):747–757 (2000).

Moskal et al., "Operation and Photodynamic Therapy for Pleural Mesothelioma: 6–Year Follow–up", *Ann Thorac Surg.*, 6–:1128–1133 (1998).

Nseyo et al., "Dihematoporphyrin Ether Clearance in Primate Bladders", *J. Urol.*, 360:1363–1366 (1986).

Nseyo et al., "Photodynamic Therapy in the Management of Resistant Lower Urinary Tract Carcinoma", *Cancer*, 60:3113–3119 (1987).

Nseyo et al., "Photodynamic Therapy (PDT) in the Treatment of Patients with Resistant Superficial Bladder Cancer: A Long Term Experience", *J. Clin. Laser Med. Surg.*, 16(1):61–68 (1998).

Pandey et al., "Alkyl Ether Analogs of Chlorophyll–a Derivatives: Part 1. Synthesis, Photophysical Properties and Photodynamic Efficacy", *Photochem. Photobiol.*, 64(1):194–204 (1996).

Pandey et al., "Chlorin and Porphyrin Derivatives as Potential Photosensitizers in Photodynamic Therapy", *Photochem. Photobiol.*, 53(1):65–72 (1991).

Pandey et al., "Comparative in vivo Sensitizing Efficacy of Porphyrin and Chlorin Dimers Joined with Ester, Ether, Carbon_Carbon or Amide Bonds", *J. Mol. Recognition*, 9(2):118–122 (1996).

Pandey et al., "Evaluation of New Benzoporphyrin Derivative with Enhanced PDT Efficacy", *Photochem. Photobiol.*, 62(4):764–768 (1995).

Pandey et al., "Fast Atom Bombardment Mass Spectral Anlayses of Photofrin II and its Synthetic Analogs", *Biomed. Environ. Mass Spect.*, 19:405–414 (1990).

Pandey et al., "Porphyrin Dimers as Photosensitizers in Photodynamic Therapy", *J. Med. Chem.*, 33:2032–2038 (1990).

Pandey et al., "Synthesis, Photophysical Properties, in Vivo Photosensitizing Efficacy, and Human Serum Albumin Binding Properties of Some Novel Bacteriochlorins", *J. Med. Chem.*, 40:2770–2779 (1997).

Pandey et al., "Syntheses and Photosensitizing Activity of Porphyrins Joined with Ester Linkages", *Cancer Res.*, 49:2042–2047 (1989).

Pandey et al., "Synthesis and Photosensitizing Activity of a Di–Porphyrin Ether", *Photochem. Photobiol.*, 47(6):769–777 (1988).

Potter et al., "Parabolic Quantitative Structure–Activity Relationships and Photodynamic Therapy: Application of a Three–Compartment Model with Clearance to the In Vivo Quantitative Structure–Activity Relationships of a Congeneric Series of Pyropheophorbide Derivatives Used as Photosensitizers for Photodynamic Therapy", *Photochem. Photobiol.*, 70(5):781–788 (1999).

Potter et al., "The Theory of Photodynamic Therapy Dosimetry: Consequences of Photo–Destruction of Sensitizer", *Photochem. Photobiol.*, 46(1):97–101 (1987).

Runfola et al., "Photodynamic Therapy for Residual Neoplasms of the Perianal Skin", *Dis Colon Rectum*, 43:499–502 (2000).

Schuh et al., "Photodynamic Therapy for Palliation of Locally Recurrent Breast Carcinoma", *J. Clin. Oncol.*, 5(11):1766–1770 (1987).

Takita et al., "Intracavitary Photodynamic Therapy for Malignant Pleural Mesothelioma", *Seminars Surg. Oncol.*, 11:368–371 (1995).

Tsuchida et al., "Correlation between Site II–Specific Human Serum Albumin (HSA) Binding Affinity and Murine in vivo Photosensitizing Efficacy of Some Photofrin Components", *Photochem. Photobiol.*, 66(2):224–228 (1997).

Vincent et al., "Hematoporphyrin Derivative in the Diagnosis and Treatment of Lung Cancer", *Adv. Exp. Med. Biol.*, 160:41–46 (1983).

Wilson et al., "Photodynamic Therapy for the Treatment of Basal Cell Carcinoma", *Arch Dermatol.*, 128:1597–1601 (1992).

Zheng et al., "A Simple and Short Synthesis of Divinyl Chlorophyll Derivatives", *J. Org. Chem.*, 64:3751–3754 (1999).

Zheng et al., "Photosensitizers Related to Purpurin–18–N–alkylimides: A Comparative in vivo Tumoricidal Ability of Ester Versus Amide Functionalities", *Bioorg. Med. Chem. Letts.*, 10:123–127 (2000).

Zheng et al., "Synthesis, Photophysical Properties, Tumor Uptake, and Preliminary in Vivo Photosensitizing Efficacy of a Homologous Series of 3–(1'–Alkyloxy)ethyl–3–devinylpurpurin–18–N–alkylimides with Variable Lipophilicity", *J. Med. Chem.*, 44:1540–1559 (2001).

Beems et al., Photosensitizing properties of bacteriochlorophyllin a and bacteriochlorin a, two derivatives of bacteriochlorophyll a, Photochem. Photobiol. 46(5): 639–643 (1987).

Bellnier et al., Murine pharmacokinetics and antitumor efficacy of the photodynamic sensitizier 2-[1-hexyloxyethyl]-2-devinyl pyropheophorbide-a, J. Photochem. Photobiol. B: Biol. 20: 55–61 (1993).

Dictionary of Cell Biology, Second Edition (Lackie & Dow, eds., 1989), p. 17.

Dougherty, T.J., Photosensitization of malignant tumors, Seminars in Surgical Oncology 2:24–37 (1986).

Gagel, M. P., Photodynamic therapy with porphyrins (1997), available at http://www.dermatology.org/laser/pdt.html.

Henderson et al., An in vivo quantitative structure–activity relationship for a congeneric series of pyropheophorbide derivatives as photosensitizers for photodynamic therapy, Cancer Research 57: 4000–4007 (1997).

Kessel et al., Photosensitization with bacteriochlorins, Photochem. Photobiol. 58(2): 200–203 (1993).

Kozyrev et al., Effect of substituents in $OsO_4$ reactions of metallochlorins regioselective synthesis of isobacteriochlorins and bacteriochlorins, Tetrahedron Letters 37(22): 3781–3784 (1996).

Marcus, S. L., Photodynamic therapy of human cancer, Proc. of the IEEE 80(6): 869–889 (1992).

Merck Manual of Diagnosis and Therapy, 17th edition (Beers & Berkow, eds., 1999), pp. 816–817 and 1654–1657.

Pandey et al., Comparative in vivo sensitizing efficacy of porphyrin and chlorin dimers joined with ester, ether, carbon–carbon or amide bonds, J. Molecular Recognition 9: 118–122 (1996).

Rimington et al., Preparation and postsensitizing properties of hematoporphyrin ethers, Free Rad. Res. Comms. 7(3–6): 139–142 (1989).

Rungta et al., Purpurinimides as photosensitizers: effect of the presence and position of the substituents in the in vivo photodynamic efficacy, Bioorg. Medicinal Chem. Letters 10: 1463–1466 (2000).

Schmidt–Erfurth et al., In vivo uptake of liposomal benzoporphyrin derivative and photothrombosis in experimental corneal neovascularization, Lasers in Surgery and Med. 17: 178–188 (1995).

Spikes, J.D., Porphyrins and related compounds as photodynamic sensitizers, Annals of the New York Academy of Sciences 244: 496–508 (1975).

Stedman's Medical Dictionary, 26th Edition, (Williams & Wilkens, 1995), pp. 268, 276–280, 726–727, 1165, 1182, and 1571–1572.

Su, F., Photodynamic Therapy: A Maturing Medical Technology, OE–Reports, SPIE, Feb. 2000, available at http://www.spie.org/web/oer/february/feb00/phototheapy.html.

Taber's Cyclopedic Medical Dictionary, 14th edition (C. L. Thomas, ed., 1983), p. 63.

Woodburn et al., Evaluation of porphyrin characteristics required for photodynamic therapy, Photochem. Photobiol. 55(5): 697–704 (1992).

Bellnier et al., "Murine pharmacokinetics and antitumor efficacy of the photodynamic sensitizer 2-[1-hexyloxyethyl]-2-devinyl pyropheophorbide-a", *J. Photochem. Photobiol. B: Biol.*, 20:55–61 (1993).

Gust et al., "Triplet and Singlet Energy Transfer in Carotene–Porphyrin Dyads: role of the Linkage Bonds", *J. Am. Chem. Soc.*, 114:3590–3603 (1992).

Jurgens et al., "Reaktionen von Chlormethyl(methyl)ether mit Chlorin–Derivaten", *Liebigs Ann. Chem.*, Heft 12: 1992–2004 (1979).

Kerrigan et al., "Carotenoporphyrins in cancer diagnosis and phototherapy", *Dissertation Abstracts International*, 54(7):3624–B (1994).

Kozyrev et al., "Syntheses of Stable Bacteriochlorophyll–a Derivatives As Potential Photosensitizers For Photodynamic Therapy", *Tetrahedron Letts*, 37(36):6431–6434 (1996).

Nilsson et al., "Laser–induced fluorescence studies of the biodistribution of carotenoporphyrins in mice", *British J. of Cancer*, 76(3):355–364 (1997).

Pandey et al., "Structure/Activity Relationships Among Photosensitizers Related To Pheophorbides And Bacteriopheophorbides", *Bioorganic & Medicinal Chem. Letts.*, 2(5):491–496 (1992).

Pandey et al., "Improved photosensitizers for phtodynamic therapy", SPIE, 1645:264–273 (1992).

* cited by examiner

Bacteriochlorin
(780 nm)

Chlorin
(660 nm)

LONG WAVE LENGTH ABSORBING BACTERIOCHLORIN ALKYL ETHER ANALOGS

BACKGROUND OF THE INVENTION

This invention relates to compounds for treatment and detection of hyperproliferatve tissues such as tumors using photodynamic methods. These compounds have the ability to preferentially collect in such tissues when injected into an organism and absorb light either to cause reduction in growth of the tissue, such as by its destruction, or to cause emission of energy from the tissue that can be detected to locate the tissue. Such reduction and detection using photodynamic compounds is collectively referred to herein as photodynamic therapy.

Photodynamic therapy (PDT) is a relatively new modality for the treatment of various types of solid tumors. Many porphyrins and related photosensitive compounds demonstrate the ability to selectively accumulate in neoplastic tissue after intravenous injection and sensitize the tissue to photoirradiation. Activation of the photosensitive agent by visible light, delivered by a laser through fiber optics, results in the generation of cytotoxic agents. It is currently accepted that the production of singlet oxygen, formed from molecular oxygen, formed from molecular oxygen by the transfer of energy directly or indirectly from the activated photosensitizer, is responsible for tumor homeostasis and the observed tumor destruction.

Following absorption of light, the photosensitizer is transformed from its ground singlet state (P) into an electronically excited triplet state ($^3P^*$; $\tau \sim 10^{-2}$ sec.) via a short-lived excited singlet state ($^1P^*$; $\tau \sim 10^{-6}$ sec.) The excited triplet can undergo non-radiative decay or participate in an electron transfer process with biological substrates to form radicals and radical ions, which can produce singlet oxygen and superoxide ($O_2^-$) after interaction with molecular oxygen ($O_2$). Singlet oxygen is the key agent responsible for cellular and tissue damage in PDT, causing oxidation of the target tissue (T); there also is evidence that superoxide ion may be involved.

In 1978, it was reported that a combination of hematoporphyrin derivative (HpD) and light was effective in causing partial or complete tumor necrosis in 111 of 113 tumors in 25 patients. PDT with Photofrin®, a purified HpD, has been approved in Canada for bladder and esophageal cancer; in the Netherlands and France for early and advanced stage esophageal cancer; in Japan for early stage lung, esophageal, gastric, and cervical cancer; and in the United States for advanced stage esophageal and lung cancers. More than 10,000 patients worldwide have been treated with PDT for a multiplicity of tumors accessible to light, including skin, lung, bladder, head and neck, breast, and esophageal cancers. Photofrin®, the current commercially used photosensitive drug, has some desirable characteristics, including good efficacy, water solubility, good yield of singlet oxygen, and ease of manufacture. However, Photofrin® has some disadvantageous properties: (i) it is a complex mixture of porphyrin dimers and higher oligomers linked by ether, ester, and/or carbon-carbon bonds and, therefore is difficult to study; (ii) it shows skin phototoxicity in patients for four to six weeks after administration; (iii) due to its relatively weak absorbance in the red region (630 nm), lack of penetration of light through tissue limits current clinical applications of Photofrin® in PDT to the destruction of cancerous tissue less than 4 mm from the source of light used in the therapy.

It has been established that both absorption and scattering of light by tissue increase as the wavelength decreases. Therefore, tissue penetration increases as the wavelength increases. Heme proteins in tissue account for most of the absorption of light in the visible region, and in tissue, light penetration drops off rapidly below 550 nm. However, there is a significant increase in penetration from 550 to 630 nm, and penetration doubles again to 700 nm. This is followed by a 10% increase in tissue penetration as the wavelength moves towards 800 nm.

Another reason that sets the ideal wavelength to 700–800 nm is the availability of the light sources in this region. Currently available laser lights used at 630 nm are expensive and not easy to handle clinically. A better solution is to use diode lasers. Advantages of diode lasers are low cost, negligible running cost, high reliability, small size and portability. Although diode lasers are now becoming available at 630 nm, photosensitizers with absorption between 700 to 800 nm in conduction with diode lasers are still desirable for treating tumors that are deeply seated. All these factors establish 700 to more than 800 nm as the optimal wavelength absorption for an efficient photosensitizer. Besides the properties discussed previously, the preferential tumor localization, stability, singlet oxygen producing efficiency, stability, low toxicity and solubility in appropriate injectable solvents are other important factors to be considered in developing an effective PDT agent.

In recent years, a number of long wavelength (>650 nm) absorbing photosensitizers have been reported as potential candidates for achieving maximum tissue penetration. Among such compounds, some naturally occurring bacteriochlorophylls have been reported as effective photosensitizers in preliminary in vitro and in vivo studies. However, most of the naturally occurring bacteriochlorins which have absorptions at 760–780 nm are extremely sensitive to oxidation, which results in a rapid transformation into the chlorin state which has an absorption maximum at or below 660 nm (see FIG. 1). Furthermore, if a laser is used to excite the bacteriochlorin in vivo, oxidation may result in the formation of a new chromophore absorbing outside the laser window, which reduces the photosensitizing efficacy. In order to render PDT more generally applicable to tumor therapy, there is need for long wavelength absorbing photosensitizers, such as, stable bacteriochlorins, which should also be able to localize in relatively high concentration at the tumor site related to normal tissues.

It is therefore an object of the invention to develop a stable photosensitizer that preferentially absorbs into hyperproliferative tissue and absorbs light efficiently at a wavelength of from about 700 to about 850 nm.

It is a further object of the invention to provide a method for photodynamic therapy using such stable photosensitizers.

BRIEF DESCRIPTION OF THE INVENTION

Figure 1:
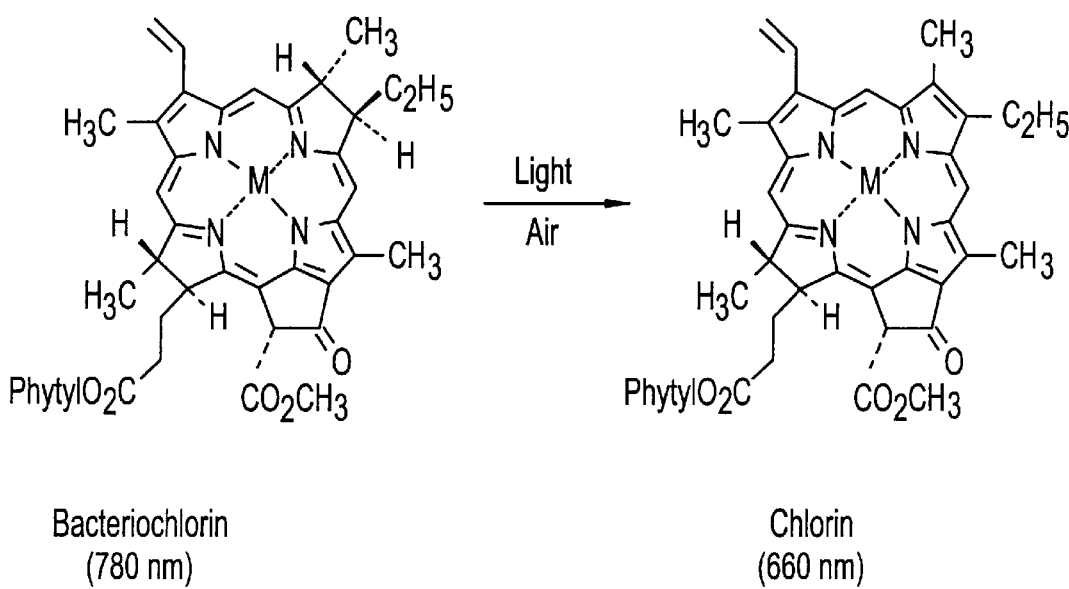
FIG. 1 shows a structural equation showing transformation of bacteriochlorin into chlorin.

In accordance with the invention novel compounds are therefore provided that either preferentially absorb into hyperproliferative tissue and absorb light efficiently at a wavelength of between about 700 and about 850 nm or act as intermediates for such absorbing compounds.

More particularly, the compounds of the invention have the formula:

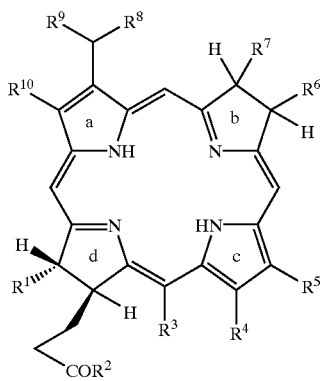

where $R^1$, $R^5$, $R^9$, and $R^{10}$ are independently lower alkyl of 1 to 3 carbon atoms provided that at least three of $R^1$, $R^5$, $R^9$, and $R^{10}$ are methyl; $R^2$ is —OH, —$OR^{11}$, —$NHR^{11}$, aryl, or -aminoacid; $R^3$ and $R^4$ are independently —$COR^{11}$ or taken together are

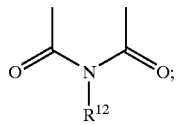

$R^6$ and $R^7$ are independently lower alkyl of 1 to 3 carbon atoms; $R^8$ is O-alkyl of 1 to about 12 carbon atoms and usually 1 to 8 carbon atoms, S-alkyl of 1 to about 12 carbon atoms and usually 1 to 8 carbon atoms, —O-aryl, or —O-heterocyclic ring of 5 or 6 carbon atoms; $R^{11}$ is alkyl of 1 to 6 carbon atoms; and $R^{12}$ is lower alkyl of 1 to about 12 carbon atoms, aryl, or aminoalkyl of 1 to 8 carbon atoms; provided that at least one of $R^8$, $R^{11}$, and $R^{12}$ is hydrophobic and together contain at least 10 carbon atoms.

Especially suitable absorbing compounds of the invention have at least one pendant group sufficiently hydrophobic to cause the compound to enter hyperproliferative tissue. Such pendant group usually includes an aliphatic or aromatic structure containing at least two carbon atoms and, when acting as the primary hydrophobic moiety, usually contains at least seven carbon atoms. The compound may have more than one pendant hydrophobic group.

Examples of specific structures that are able to preferentially collect in hyperproliferative tissue are those compounds wherein $R^2$ is —$OR^{11}$ and $R^{11}$ is n-alkyl of 3 to about 10 carbon atoms, e.g. n-propyl; those compounds wherein $R^3$ and $R^4$ taken together are

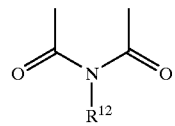

where $R^{12}$ is alkyl of 3 to about 10 carbon atoms, e.g. n-hexyl; and those compounds where $R^8$ is O-alkyl of 3 to about 10 carbon atoms, e.g. n-heptyl.

In preferred compounds of the invention, $R^1$, $R^5$, $R^7$, $R^9$, and $R^{10}$ are all methyl and $R^6$ is ethyl.

The invention also includes the methods for treating and detecting hyperproliferative tissue such as tumors, by exposing the tissue to an amount of the absorbing compound of the invention which is effective for detecting or reducing the growth of the tissue upon exposure to sufficient light at a wave length between 700 and 850 nm.

In a preferred embodiment, the invention further includes facile approaches for the preparation of bacteriopurpurin-18-N-alkyl imides and their conversion into the corresponding 3-deacetyl-3-alkylether analogs with carboxylic acid, ester or amide functionalities and for the preparation of bacteriochlorin $p_6$ and its conversion into a series of alkyl ether analogs with carboxylic acid, ester or amide functionalities. The invention also includes use of these novel bacteriochlorins for the treatment of cancer or other non-oncological diseases by photodynamic therapy.

The compounds of the invention are unique in that they are bacteriochlorins, i.e., they have diagonally opposite fused reduced pyrrol rings (rings b and d) and have an alkyl ether group attached to the "a" fused pyrrol ring. The compounds of the invention have peak light absorbance at a wave length of between about 700 and about 850 nm and usually between 750 and 825 nm. The compounds further are uniquely stable due to the presence of an electron withdrawing group attached to the "c" fused pyrrol ring. The electron withdrawing group is preferably a stable six member fused imide ring, or the substituent $R_4$ on ring "c" is the radical —$COR^{11}$ where $R^{11}$ is —OH; —O-alkyl of 1 to about 10 carbon atoms; —NH-alkyl of 1 to about 12 carbon atoms; aryl, electron withdrawing at its position of attachment; or an amino acid radical.

The compounds of the invention suitable for injection into a mammal for preferential accumulation in hyperproliferative tissue also have at least one and preferably at least two pendant hydrophobic groups that assist in causing the compound to enter the hyperproliferative tissue.

"Hyperproliferative tissue" as used herein means tissue that grows out of control and includes tumors and unbridled vessel growth such as blood vessel growth found in age related macular degeneration.

In using compounds of the invention for photodynamic therapy, the compounds are usually injected into the mammal, e.g. human, to be diagnosed or treated. The level of injection is usually between about 0.1 and about 0.5 μmol/kg of body weight. In the case of treatment, the area to be treated is exposed to light at the desired wave length and energy, e.g. from about 100 to 200 J/cm². In the case of detection, fluorescence is determined upon exposure to light at the desired wave length. The energy used in detection is sufficient to cause fluorescence and is usually significantly lower than is required for treatment.

The invention includes a method for preparing compounds of the invention without requiring complex and inefficient synthesis steps.

For the preparation of bacteriopurpurin 1 (FIG. 2), the n-propyl alcohol extract of Rb Sphaeroides, which contains bacteriochlorophyll-a ($\lambda_{max}$ 774 nm), was directly reacted with KOH/n-propanol in presence of air. It was immediately treated with HCl or $H_2SO_4$ (pH 2 to 3) to produce bacteriopurpurin-18 propyl ester and the related carboxylic acid 2 which in reacting with $H_2SO_4$/n-propanol can be converted into the related propyl ester analog 1. Compared to the naturally occurring bacteriochlorophyll-a, bacteriopurpurin with a fused anhydride ring system 2 (813 nm) was found to be extremely stable at room temperature. However, it was found to be unstable in vivo.

Compared to the anhydride ring system, compounds with fused imide ring system in other compounds have shown stability in vivo. For example, among non-porphyrin systems, amonafide, an imide derivative and its structural analogs are reported as anti-neoplastic agents in vitro as well as in vivo with good stability. While we could not know how this might apply to non-porphyrin systems, we investigated the effect of such cyclic structures in the bacteriochlorin system. Initially we followed our own methodology developed for the preparation of purpurin-18-N-alkylimides (U.S. Pat. No. 5,952,366 incorporated herein by reference). Unfortunately, that approach produced a complex reaction mixture. Thus, in a modified approach, bacteriopurpurin-a 2 was first reacted with an alkyl amine (e.g. n-hexyl amine). The formation of the intermediate amide was monitored by spectrophotometry and analytical thin layer chromatography. The intermediate amide analog 3, obtained as a mixture of two isomers, was reacted with diazomethane, and the solvent was removed under vacuum. The residue so obtained was re-dissolved in tetrahydrofuran, and solvent was evaporated. This procedure was repeated several times until the disappearance of the absorption at 765 nm and appearance of a new peak at 822 nm. The bacteriochlorin-N-hexylimide so obtained had the required spectroscopic characteristic necessary for an "ideal" photosensitizer, and was stable in vitro and in vivo, but unfortunately did not produce any significant in vivo PDT efficacy.

Figure 2:
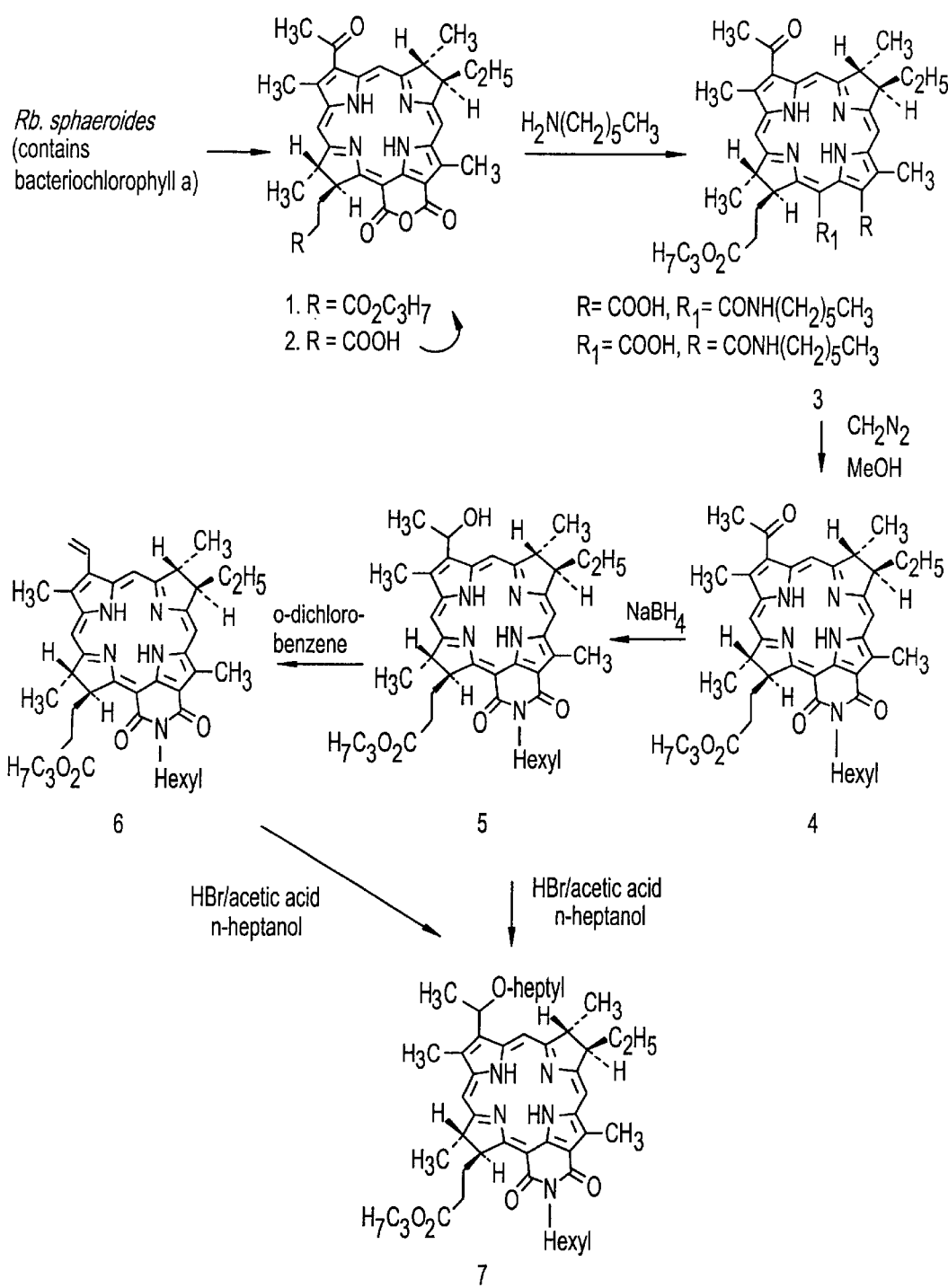
FIG. 2 shows a structural equation for the preparation of 3-alkyl ether bacteriopurpurin-imide.

Our next step was to investigate the effect of alkyl ether substitutions in bacteriochlorin series since similar substitutions in non-bacteriochlorin systems sometimes enhanced tumor localization see e.g. U.S. Pat. Nos. 5,459,159 and 5,952,366 both of which are incorporated herein by reference. In order to introduce various alkyl ether substituents at the peripheral position, the bacteriopurpurinimide 4 containing an acetyl group at position 3 was first reduced to the corresponding 3-(1-hydroxyethyl) 5 by reacting with sodiumborohydride in excellent yield, which on dehydration by refluxing in o-dichlorobenzene for 5 min produced the vinyl analog 6 in >80% yield. For the preparation of the desired alkyl ether analog, the hydroxy analog 5 was treated with HBr/acetic acid, and the intermediate bromo- derivative was immediately reacted with various alkyl alcohols, and the corresponding alkyl ether analogs (e.g. 7) were isolated in about 70% yield. Under similar reaction conditions, the vinyl bacteriopurpurin-imide 6 also produced the desired alkyl ether derivatives, but in low yield (FIG. 2).

Figure 3:
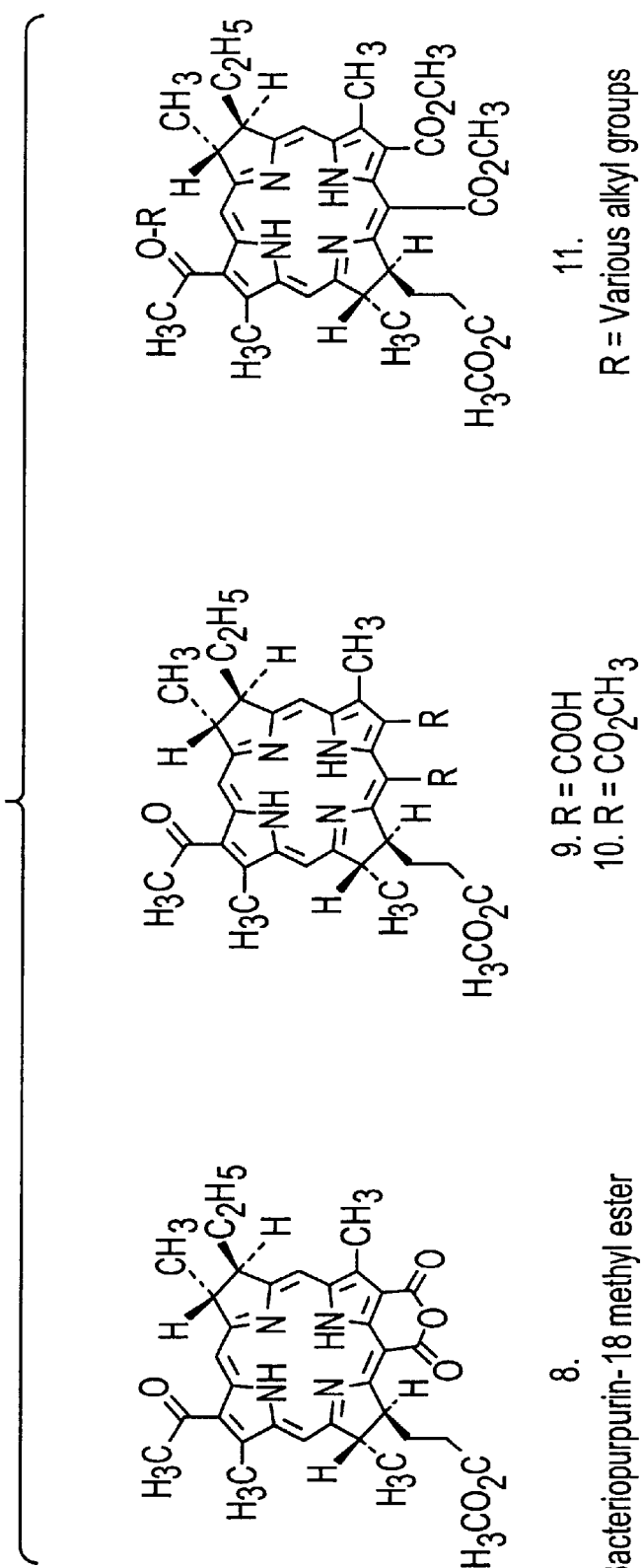
FIG. 3 shows the structural formulas of compounds 8, 9, 10 and 11.
Figure 4A:
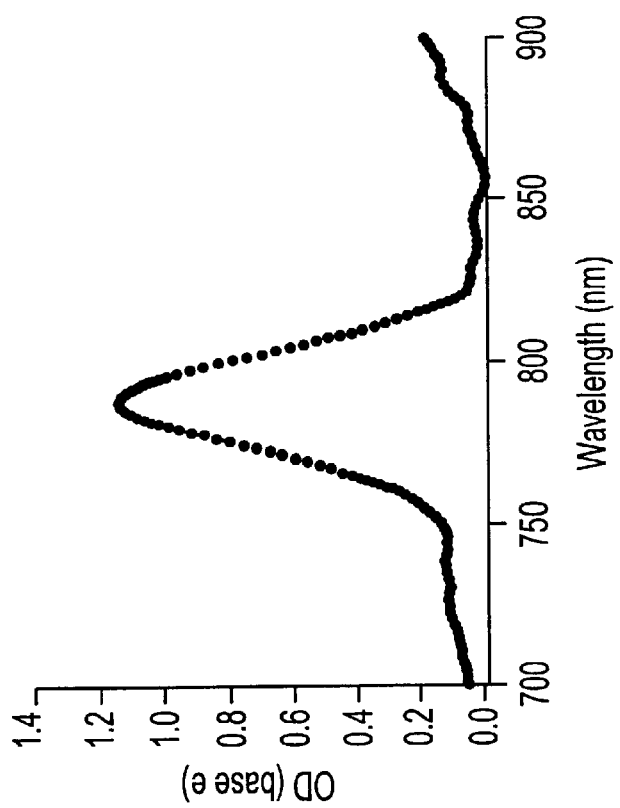
FIGS. 4A and 4B show curves of in vivo light wave absorption of compound 7 in RIF tumor at 24 hours and 5 days post injection.
Figure 4B:
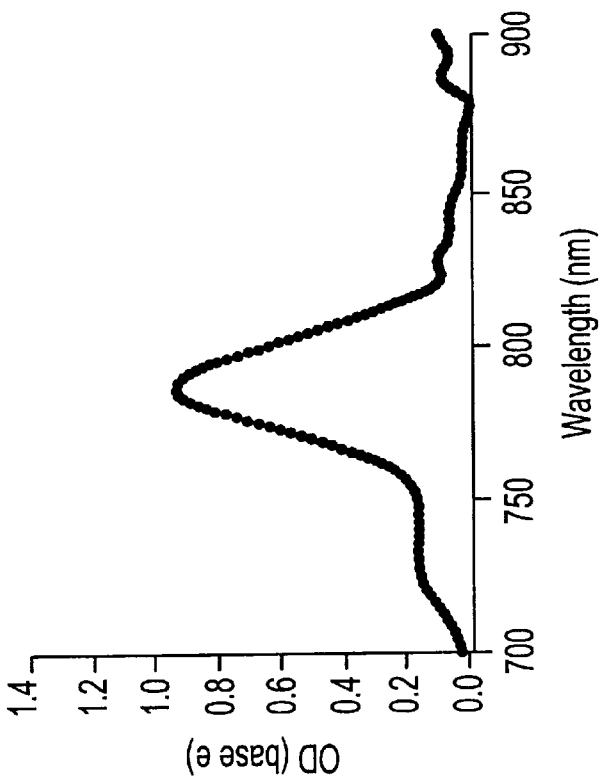

This invention also deals with the synthesis of the alkyl ether analogs of bacteriopurpurin $p_6$ and their amide derivatives ($\lambda_{max}$ 760 nm). For the preparation of these compounds, bacteriopurpurin-18 methyl ester 8 was reacted with aqueous sodium carbonate or sodium hydroxide/THF solution. The dicarboxylic acid 9 obtained by the cleavage of the fused anhydride ring system was converted into the corresponding methyl ester 10 upon reacting with diazomethane. Reaction of 10 with sodium borohydride and subsequent treatment with HBr/acetic acid and various alkyl alcohols will generate the desired alkyl ether derivatives 11 (FIG. 3). The regiospecific hydrolysis of the propionic ester functionality into the corresponding carboxylic acid and subsequent conversion into various amides could generate a series of amide analogs.

The following examples serve to illustrate and not limit the present invention; melting points are uncorrected and were measured on a Fisher Johns melting point apparatus. Electronic absorption spectra were measured on a Genesis 5 spectrophotometer. Mass spectra were measured at the Department of Molecular and Cellular Biophysics, RPCI, Buffalo. NMR spectra were obtained with a 400 MHz Bruker instrument at the NMR facility of the institute. Samples were dissolved in $CDCl_3$ and the chemical shifts are expressed in δ ppm relative to $CHCl_3$ at 7.258 ppm. Analytical thin layer chromatography was used to monitor the reactions and to check the purity of the desired compounds on cut strips of Merck or Whatman silica gel 60F254 precoated (0.25 mm thickness) plastic backed sheets. For column chromatography Silica gel (70–230 mesh) was used for normal gravity column.

Tetrahydrofuran (THF) was distilled over sodium, and dichloromethane over calcium hydride before use. The phrase "dried, filtered and evaporated" means drying over sodium sulfate, filtering through glass wool, and then evaporating off the solvent using a Buchi rotary evaporator under house vacuum or high vacuum achieved with an oil pump.

EXAMPLE 1

Preparation of 3-Acetyl-bacteriopurpurin-18-propyl Ester 1

Rb sphaeroides, (350 gram) was dissolved in ether (200 ml) and pyridine (10 ml). Sodium hydroxide (12 g) dissolved in n-propanol (100 ml) was added, and a stream of air was bubbled through the solution with constant stirring for 2 h. The ethereal layer was removed, and the pH of the aqueous phase was adjusted by adding $H_2SO_4$ to 2.5. The solvent was removed under vacuum. The residue so obtained was redissolved in THF and evaporated. This process was repeated several times until the peak at 765 disappeared, and a new peak appeared at 804 nm. After removing the solvent the residue was found to be a mixture of two compounds and separated by column chromatography. The faster moving band was identified as the title product, whereas the slower moving band was characterized as the related carboxylic acid analog, which on treating with 5% sulfuric acid/n-propanol produced the corresponding propyl ester. Yield: 250 mg.

EXAMPLE 2

Preparation of 3-Acetyl-bacteriopurpurin-18-N-hexylimide 4

Bacteriopurpurin-18 propyl ester 1 (200 mg) was dissolved in dichloromethane (10 ml) and n-hexylamine (0.5 ml) was added. The reaction was stirred at room temperature overnight. The reaction was monitored by TLC and spectrophotometry (disappearance of a peak at 804 nm and appearance of a new peak at 765 nm). The solvent was removed under high vacuum, and the residue was dissolved in dichloromethane. It was then treated with diazomethane to convert the carboxylic acid functionality into the corresponding methyl ester. THF was then added, and solvent was removed under vacuum until the intensity of the amide peak at 760 reduced to 10% and a new peak caused by the formation of the title compound appeared at 822 nm. It was then purified by silica column chromatography using 2% acetone/dichloromethane as eluent. The residue obtained after evaporating the solvent was precipitated with dichloromethane/hexane mixture. Yield: 112 mg. NMR (δ ppm, CDCl$_3$): 9.31 (s, 1H, 5-H); 8.80 (s, 1H, 20-H); 5.29 (d, 1H, 17-H); 4.42 (t, 2H, hexylimide-a-CH$_2$); 4.29 (m, H, 3-H); 4.09 (m, 3H, CO$_2$CH$_2$ and 18-H); 3.94 (m, 2H, 7-H and 8-H); 3.70 (s, 3H, 12-Me); 3.55 s, 3H, 2-Me); 3.17 (s, 3H, 3-Me); 2.68 (M, 1H, 17b-H); 2.41 (m, 5H, CH$_2$CH$_2$CH$_3$+8a-CH$_2$+7b'H); 2.04 (m, 4H, 17a-H, 17a'-H and b, c-N-hexyl-CH$_2$); 1.70, 1.67 (each d, 3H, 18-Me and 7-Me); 1.32 (m, 4H, d,e-hexylimide-CH$_2$); 1.14 (t, 3H, 3-b Me); 0.93 (t, 3H, CH$_2$CH$_2$CH$_3$); −0.53 and −0.75 (each br s, 2H, 2NH). Mass calculated for C$_{42}$H$_{53}$N$_5$O$_5$: 707. Found: 707.9 (M+1). Long wavelength absorption λ$_{max}$ 822 nm.

EXAMPLE 3

Preraration of 3-Deacetyl-3-(1-hydroxyethyl) bacteriopurrurin-18-N-hexylimide 5

The foregoing bacteriopurpurin-imide 4 (100 mg) was dissolved in dichloromethane (10 ml) and methanol (5 ml). Sodium borohydride (30 mg) was added slowly (within 30 min) with continuous stirring at 0° C. The reaction was monitored by TLC and spectrophotometry (appearance of a new peak at 786 nm). It was then diluted with dichloromethane. The organic layer was washed with 5% acetic acid and again with water. It was dried over sodium sulfate. Evaporation of the solvent gave the desired product, 80 mg. NMR (δ ppm, CDCl$_3$): 8.81 (d, 1H, 5-H); 8.00 (s, 1H, 20-H); 8.25 (d, 1H, 17-H); 6.18 (q, 1H, CH(OH)CH$_3$); 4.42 (t, 2H, hexylimide-a-CH$_2$); 4.29 (m, H, 3-H); 3.94 (m, 7H and 8-H); 3.82 (m, 3H, CO$_2$CH$_2$ and 18-H); 3.60 and 3.20 (each s, 3H, 3-Me); 2.68 (m, 1H, 17b-H); 2.41 (m, 5H, CH$_2$CH$_2$CH$_3$+8a-CH$_2$+7b'H); 2.04 (m, 4H, 17a-H, 17a'H and b, c-N-hexyl-CH$_2$); 2.10 (d, 3H, 18-Me); 1.80 (m, 2H, 8-CH$_2$CH$_3$) and 1.75–1.30 (m, 4H, d,e-hexylimide-CH$_2$); 1.10. 0.93 and 0.759 (total 9H: t, 3H, 3-b Me), (t, 3H, CH$_2$CH$_2$CH$_3$); −0.03 and −0.45 (each br s, 2H, 2NH). Mass calculated for C$_{42}$H$_{55}$N$_5$O$_5$: 709. Found: 709.9 (M+1). Long wavelength absorption$_{max}$ 786 nm.

EXAMPLE 4

Preparation of 3-Deacetyl-3-vinyl-bacteriopurpurin-18-N-hexylimide Propylester 6

The hydroxy analog 5 (20 mg) was added to refluxing o-dichlorobenzene (5 ml), and the solution was stirred for 5 min. It was then cooled to room temperature. The solution was passed through a silica column, eluted first with hexane to remove the o-dichlorobenzene and then with 2% acetone in dichloromethane. Evaporation of the major band gave a residue, which was crystallized from dichloromethane/hexane in 70% yield. NMR (δ ppm, CDCl$_3$): 8.61 (d, 1H, 5-H); 8.42 (s, 1H, 20-H); 8.38 (d, 1H, 17-H); 7.75 (m, 1H, CH═CH$_2$); 6.18, 6.08 (each d, 1H, CH═CH$_2$); 4.42 (t, 2H, hexylimide-a-CH$_2$); 4.29 (m, H, 3-H); 3.94 (m, 2H, 7-H and 8-H); 3.82 (m, 3H, CO$_2$CH$_2$ and 18-H); 3.60 (s, 3H, 3-Me); 3.22 (s, 3H, CH$_3$); 2.62 (m, 1H, 17b-H); 2.31 (m, 5H, CH$_2$CH$_2$CH$_3$+8a-CH$_2$+7b'H); 2.04 (m, 4H, 17a-H, 17a'H and b, c-N-hexyl-CH$_2$); 1.78 and 1.62 (each d, 3H, 18-Me and 7-Me); 1.80 (m, 2H, 8-CH$_2$CH$_3$) and 1.65–1.30 (m, 4H, d,e-hexylimide-CH$_2$); 1.10 0.93 and 0.80 (total 9H: t, 3H, 3-b Me), (t, 3H, CH$_2$CH$_2$CH$_3$); −0.03 and −0.40 (each brs. 2H, 2NH). Mass calculated for C$_{42}$H$_{53}$N$_5$O$_4$: 691. Found: 691.7 (M+1). Long wavelength absorption λ$_{max}$ 788 nm.

EXAMPLE 5

Preparation of 3-Deacetyl-3-(1-heptyloxyethyl)-bacteriopurpurin-N-hexylimide Propyl Ester 7

The foregoing bacteriopurpurin 5 (30 mg) was reacted with 30% HBr/acetic acid (1.5 ml) at room temperature for 2 h. The solvents were removed under high vacuum. The residue so obtained was dissolved in dry dichloromethane (5 ml) and immediately reacted with n-heptanol (1 ml). A small amount of anhydrous potassium carbonate was added before leaving the reaction at room temperature under an inert atmosphere for 45 min. It was then diluted with dichloromethane. After the standard work-up, the residue was purified by silica column chromatography. Yield 20 mg. NMR (δ ppm, CDCl$_3$): 8.82 (d, 1H, 5-H); 8.62 (s, 1H, 20-H); 8.30 (d, 1H, 17-H); 5.60 (q, 1H, CH(O-heptyl)CH$_3$); 5.25 (m, H, 17-H); 4.42 (t, 2H, hexylimide-a-CH$_2$); 4.20 (m, 3H, CO$_2$CH$_2$ and 18-H); 3.94 (m, 2H, 7-H and 8-H); 3.80 (m, O—CH$_2$ of heptyl ether chain); 3.65 (s, 3H, 3-Me); 3.25 (s, 3H, CH$_3$); 2.62 (m, 1H, 17b-He); 2.31 (m, 5H, CH$_2$CH$_2$CH$_3$+8a-CH$_2$+7b'H); 2.00–0.75, several multiplets: (m, 4H, 17a-H, 17a'H and b, c-N-hexyl-CH$_2$); 1.80 and 1.52 (each d, 3H, 18-Me and 7-Me); 1.80 (m, 2H, 8-CH$_2$CH$_3$) and 1.65–1.30 (m, 4H, d,e-hexylimide-CH$_2$ and 8H of the O-heptyl side chain); 1.10, 0.93 and 0.80 (total 12H: t, 3H, 3-b Me and O-heptyl-Me) and (t, 3H, CH$_2$CH$_2$CH$_3$); −0.03 and −0.40 (each brs, 2H, 2NH). Mass calculated for C$_{49}$H$_{69}$N$_5$O$_5$: Calculated: 807. Found: 808.3 (M+1). Long wavelength absorption λ$_{max}$ 786 nm.

The title compound was also obtained from the vinyl analog 6 by following the same methodology. However, the desired product was obtained in low yield.

EXAMPLE 6

Preparation of Bacteriopurpurin p$_6$ Trimethyl Ester

Bacteriopurpurin-18 methylester (50 mg) was dissolved in anhydrous THF (20 ML). Aqueous solution of sodium hydroxide or sodium carbonate was added. The reaction was stirred at room temperature until the parent peak at 804 nm disappeared. The pH was then slowly adjusted to 5, extracted with dichloromethane/THF mixture. The organic layer was washed with water, dried over anhydrous sodium sulfate, and the solvent was evaporated. The residue was converted into the corresponding methyl ester by reacting diazomethane, and purified by column chromatography (Silica gel). Yield 40 mg. NMR (δ ppm, CDCl$_3$): 9.70, 8.72, 8.60 (each s, 1H, 3-meso H); 5.00 (d, 1H, 17-H); 4.20 (m, 1H, 18-H); 3.95 (m, 2H, 7-H and 8-H); 4.12, 4.10, 3.60, 3.58, 3.50, 3.20 (each s, 3H, 3CO$_2$Me, 2Me and CO$_2$Me); 2.50–2.00 (m, 6H, 12-CH$_2$CH$_2$CO$_2$Me and 8-CH$_2$CH$_3$); 1.80 and 1.70 (each d, 3H, 7-Me and 18-Me); 1.20 (t, 3H, CH$_2$Me); −90 and −85 (each s, 1H, 2NH). Found: Long wavelength absorption λ$_{max}$ 760 nm.

EXAMPLE 7

Biological Studies

The photosensitizers were dissolved in known quantity of Tween 80 (Aldrich) surfactant and diluted by a factor of 10 with 5% dextrose solution in water to produce a final Tween 80 concentration of 1%. The solution was then filtered through a syringe filter. The concentration of the solution was determined on the basis of the extinction coefficient value of the photosensitizer at the longest wavelength absorption.

Before injecting the drug to the animals, the purity of the material was confirmed by HPLC using a Spectra-Physics system connected to a SP8 700 solvent delivery system and Kratos 757 absorption detector with a fixed wavelength at 405 or 786 nm. Two solvent systems were used in the HPLC analysis: solvent A was prepared by dissolving anhydrous dibasic sodium phosphate (1.0 g) in 400 ml water. To this was added HPLC grade methanol (600 ml). The pH of the solution was adjusted to 7.5 with phosphoric acid; and solvent B was prepared by dissolving anhydrous dibasic sodium phosphate (0.3 g) in 100 ml water, to this was added methanol (900 ml), and the pH was adjusted to 7.5 with phosphoric acid. Solvents A and B were used as gradient mode (0–10 min A, 10–40 min A–B, 40–50 min B, 50–60 min back to A). In some cases solvent B was used as isocratic mode (column reverse phase C-8, flow rate 1.5 ml/min). Prior to irradiation, the fur over grown and surrounding the tumor was removed with electric clippers. Twenty four hours after injecting the drug, the mouse was placed in a custom made aluminum holder. Standard light dose 75 mW/cm$^2$ for 30 min for a total incident light dose of 135 J/cm$^2$ from a tunable dye laser tuned to the maximum red absorption peak at 790 nm (in vivo absorption, determined by in vivo reflectance spectroscopy). Laser output was measured with a power meter.

Following light exposure, the mice were kept in groups of 5/cage and supplied with pelleted food and water ad libitum. Tumor size and gross appearance of both tumor and overlying skin was monitored daily for 90 days after photoillumination unless growth of non-responsive tumor require early sacrifice of those animals.

Bacteriopurpurin-imides 5–7 above have been evaluated for in vivo studies in a mouse tumor model system (RIF tumor). Results are summarized in Table 1. From these results it can be seen that among the compounds tested, 3-deacetyl-3-(1-heptyloxyethyl) purpurinimide-18 7 produced significant photosensitizing activity at a dose of 0.47 lmol/kg. The mice were treated with light (790 nm, 135 J/cm$^2$) after 24 h post injection of the drug (80% tumor cure on day 21 and 60% on day 90). At a higher drug dose (1.0 $\mu$mol/kg), all mice died (6/6) after the light treatment, suggesting that the drug is quite potent. The efficacy of the drug was also determined at variable drug and light doses. For example, reducing the drug dose to 0.2 mol/kg and keeping the same light dose (135 J/cm$^2$) did not show any PDT efficacy; however, at the higher light dose (175 J/cm$^2$) four out of six mice were tumor free on day 90. Under similar treatment conditions bacteriochlorins 5 and 6 did not produce any PDT efficacy.

TABLE 1

In vivo photosensitizing efficacy of bacteriopurpurinimides against RIF rumor (C$_3$H mice)

| Compound No. | Injected Dose ($\mu$mol/kg) | Light Dose (790 nm) 24 h post injection | Tumor Response (%) Day 7 | Day 21 | Day 90 |
|---|---|---|---|---|---|
| 7 | 1.00 | 135J/cm$^2$ | ALL MICE DIED | | |
|   | 0.47 | 135J/cm$^2$ | 80 | 80 | 60 |
|   | 0.2 | 135J/cm$^2$ | NO RESPONSE | | |
|   | 0.2 | 175J/cm$^2$ | 100 | 70 | 70 |
| 5 | 1.0 | 135J/cm$^2$ | NO RESPONSE | | |
| 6 | 1.0 | 135J/cm$^2$ | NO RESPONSE | | |

The tumor uptake and in vivo shift in the long wavelength absorption of the bacteriopurpurin-imide 7 was determined by in vivo reflectance spectroscopy. Bacteriopurpurinimide 7 had significantly higher tumor uptake at day 5 than day 1 post injection of the drug. Compared to in vitro absorption, the long wavelength absorption in vivo was observed at 790 nm, exhibiting a red shift of about 5 nm. Thus, the tumors were irradiated with light at that particular wavelength. This experiment also suggests that the fused imide ring system is quite stable in vivo even after 5 day post injection of the photosensitizer. In vivo studies with these and other bacteriochlorin analogs at variable treatment conditions are currently in progress.

Figure 5:
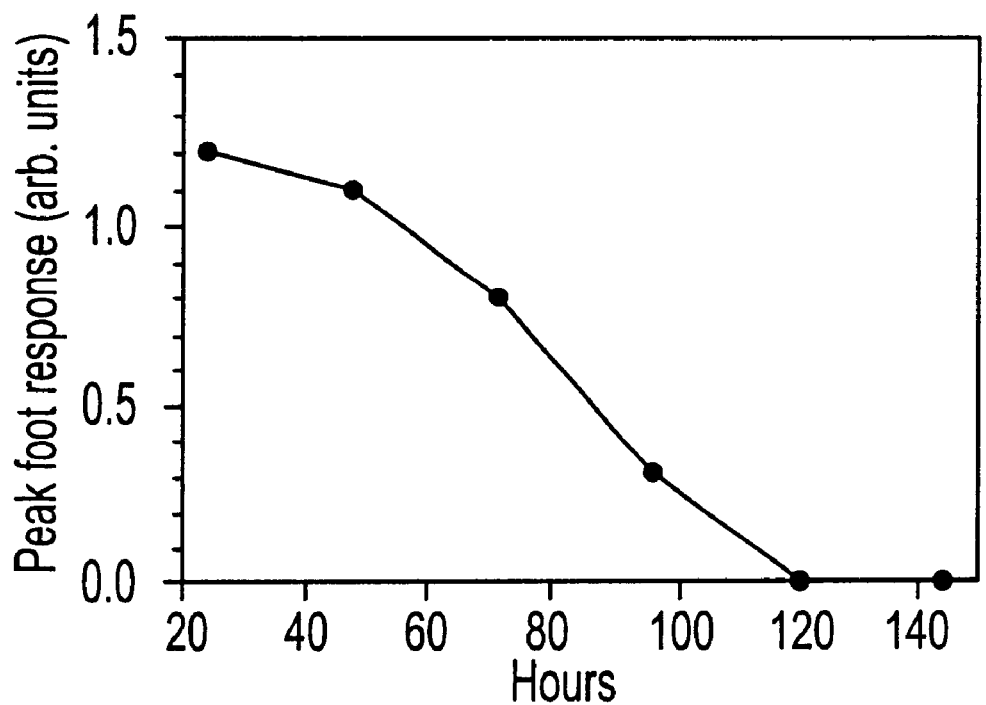
FIG. 5 is a graph showing foot response photosensitivity for compound 7.

Since prolonged cutaneous photosensitivity is a serious side-effect of Photofrin® administration, we tested the phototoxicity of 3-deacetyl-3-(1-heptyloxyethyl) bacteriopurpurin-18-N-hexylimide 7 in mouse foot tissue and the therapeutic drug and light doses. Mice were injected (I.V.) with 0.47 mmol/kg of the drug. Feet were illuminated with 135 J/cm$^2$ at 790 nm laser light on days 1, 2, 3, 4 and 5 (FIG. 5). Foot response was graded according to the following arbitrary scale: 0, no difference from normal; 0.1, very slight edema; 0.3, slight edema; 0.5, moderate edema; 0.75, large edema; 1, large edema with exudate; 1.2, moderate reddening with slight scaly or crusty appearance; 1.65, slight damage to toes; 1.75, definite damage or slight fusion of toes; 2.0, most toes fused; 2.5, foot almost shapeless with no toes; 3, only stub of foot remaining. As can be seen from FIG. 5, bacteriopurpurin-imide 7 did not show any toxicity when feet were illuminated 5 days after injection. These results suggest a possibility that this compound is cleared rapidly from mouse foot tissues, unlike Photofrin®, which showed a long term cutaneous phototoxicity.

What is claimed is:

1. A compound having the formula:

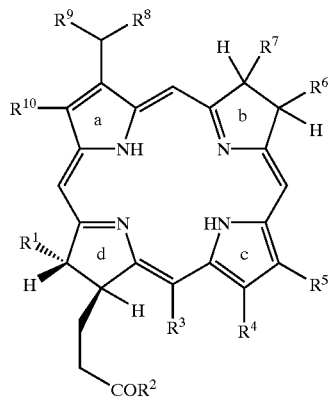

wherein:
  $R^1$, $R^5$, $R^9$, and $R^{10}$ are independently lower alkyl of 1 to 3 carbon atoms provided that at least three of $R^1$, $R^5$, $R^9$, and $R^{10}$ are methyl;
  $R^2$ is —OH, —OR$^{11}$, or —NHR$^{11}$, or aryl;
  $R^3$ and $R^4$ are independently —COR$^{11}$ or taken together are

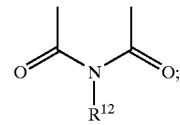

$R^6$ and $R^7$ are independently lower alkyl of 1 to 3 carbon atoms;
  $R^8$ is O-alkyl of 1 to 12 carbon atoms, S-alkyl of 1 to 12 carbon atoms or O-aryl;
  $R^{11}$ is alkyl of 1 to 6 carbon atoms; and
  $R^{12}$ is lower alkyl of 1 to 12 carbon atoms, aryl, or aminoalkyl of 1 to 8 carbon atoms, provided that $R^8$, $R^{11}$, and $R^{12}$ together contain at least 10 carbon atoms.

2. The compound of claim 1 wherein the compound has a peak light absorption at a light wave length of between about 750 and 850 nm.

3. The compound of claim 2 wherein $R^1$, $R^5$, $R^9$, and $R^{10}$ are all methyl.

4. The compound of claim 3 wherein $R^2$ is $-OR^{11}$ and $R^{11}$ is n-propyl.

5. The compound of claim 4 wherein $R^3$ and $R^4$ taken together are

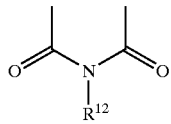

and $R^{12}$ is hexyl.

6. The compound of claim 5 where $R^6$ is ethyl and $R^7$ is methyl.

7. A compound having the formula:

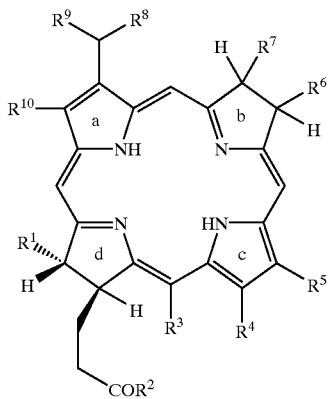

wherein:
$R^1$, $R^5$, $R^9$, and $R^{10}$ are all methyl;
$R^2$ is $-OR^{11}$ and $R^{11}$ is n-propyl;
$R^3$ and $R^4$ taken together are

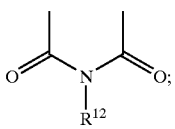

$R^6$ is ethyl and $R^7$ is methyl;
$R^8$ is O-heptyl;
$R^{12}$ is hexyl; and
the compound has a peak light absorption at a light wavelength of between about 750 and 850 nm.

8. A method of photodynamic therapy for treating hyperproliferative tissue, comprising:
administering to the subject an effective amount of the compound of claim 2, wherein the compound of claim 2 preferentially accumulates in the hyperproliferative tissue; and
exposing the area to be treated to light at the peak absorption wavelength of the compound of claim 2, whereby the hyperproliferative tissue is destroyed or its growth reduced.

9. A method of photodynamic therapy for treating hyperproliferative tissue, comprising:
administering to the subject an effective amount of the compound of claim 5, wherein the compound of claim 5 preferentially accumulates in the hyperproliferative tissue; and
exposing the area to be treated to light at the peak absorption wavelength of the compound of claim 5, whereby the hyperproliferative tissue is destroyed or its growth reduced.

10. A method of photodynamic therapy for treating hyperproliferative tissue, comprising:
administering to the subject an effective amount of the compound of claim 4, wherein the compound of claim 4 preferentially accumulates in the hyperproliferative tissue; and
exposing the area to be treated to light at the peak absorption wavelength of the compound of claim 4, whereby the hyperproliferative tissue is destroyed or its growth reduced.

11. A method of photodynamic therapy for treating hyperproliferative tissue, comprising:
administering to the subject an effective amount of the compound of claim 7, wherein the compound of claim 7 preferentially accumulates in the hyperproliferative tissue; and
exposing the area to be treated to light at the peak absorption wavelength of the compound of claim 7, whereby the hyperproliferative tissue is destroyed or its growth reduced.

12. A method for detecting the presence of hyperproliferative tissue by exposing the tissue to a sufficient quantity of the compound of claim 2 to cause a detectable light emission from the tissue, at a wave length different from the peak absorption wave length, upon exposure of the tissue to light at the peak absorption wave length.

13. A method for detecting the presence of hyperproliferative tissue by exposing the tissue to a sufficient quantity of the compound of claim 3 to cause a detectable light emission from the tissue, at a wave length different from the peak absorption wave length, upon exposure of the tissue to light at the peak absorption wave length.

14. A method for detecting the presence of hyperproliferative tissue by exposing the tissue to a sufficient quantity of the compound of claim 4 to cause a detectable light emission from the tissue, at a wave length different from the peak absorption wave length, upon exposure of the tissue to light at the peak absorption wave length.

15. A method for detecting the presence of hyperproliferative tissue by exposing the tissue to a sufficient quantity of the compound of claim 7 to cause a detectable light emission from the tissue, at a wave length different from the peak absorption wave length, upon exposure of the tissue to light at the peak absorption wave length.

16. A compound having the formula:

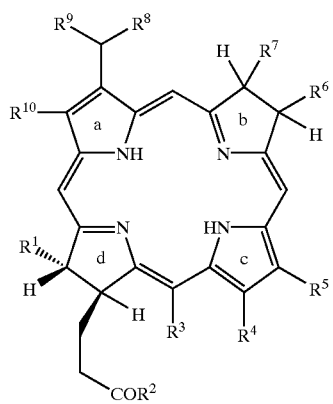

wherein:
$R^1$, $R^5$, $R^9$, and $R^{10}$ are independently lower alkyl of 1 to 3 carbon atoms provided that at least three of $R^1$, $R^5$, $R^9$, and $R^{10}$ are methyl;
$R^2$ is an amino acid group;
$R^3$ and $R^4$ taken together are

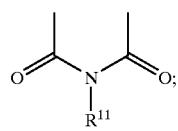

$R^6$ and $R^7$ are independently lower alkyl of 1 to 3 carbon atoms;
$R^8$ is O-alkyl of 1 to 12 carbon atoms, S-alkyl of 1 to 12 carbon atoms, or aryl; and
$R^{11}$ is lower alkyl of 1 to 12 carbon atoms, aminoalkyl of 1 to 8 carbon atoms, or aryl, provided that $R^8$ and $R^{11}$ together contain at least 10 carbon atoms.

17. A method of photodynamic therapy for treating hyperproliferative tissue, comprising:
administering to the subject an effective amount of the compound of claim 16, wherein the compound of claim 16 preferentially accumulates in the hyperproliferative tissue; and
exposing the area to be treated to light at the peak absorption wavelength of the compound of claim 16, whereby the hyperproliferative tissue is destroyed or its growth reduced.

18. A compound having the formula:

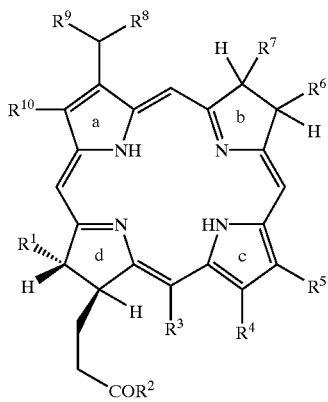

wherein:
$R^1$, $R^5$, $R^9$, and $R^{10}$ are independently lower alkyl of 1 to 3 carbon atoms provided that at least three of $R^1$, $R^5$, $R^9$, and $R^{10}$ are methyl;
$R^2$ is —OH, —OR$^{11}$, or —NHR$^{11}$, or aryl;
$R^3$ is —COR$^{11}$;
$R^4$ is —COR$^{12}$;
$R^6$ and $R^7$ are independently lower alkyl of 1 to 3 carbon atoms;
$R^8$ is O-alkyl of 1 to 12 carbon atoms, S-alkyl of 1 to 12 carbon atoms, or aryl;
$R^{11}$ is alkyl of 1 to 6 carbon atoms; and
$R^{12}$ is —OH, —O-alkyl of 1 to 10 carbon atoms, —NH-alkyl of 1 to 12 carbon atoms, or aryl, provided that $R^8$, $R^{10}$, and $R^{12}$ together contain at least 10 carbon atoms.

* * * * *

UNITED STATES PATENT AND TRADEMARK OFFICE
CERTIFICATE OF CORRECTION

PATENT NO. : 6,624,187 B1
DATED : September 23, 2003
INVENTOR(S) : Pandey et al.

It is certified that error appears in the above-identified patent and that said Letters Patent is hereby corrected as shown below:

Column 1,
Lines 25-27, please replace "It is currently accepted that the production of singlet oxygen, formed from molecular oxygen, formed from molecular oxygen by the transfer of energy directly or indirectly from the activated photosensitizer," with -- it is currently accepted that the production of singlet oxygen, formed from molecular oxygen by the transfer of energy directly or indirectly from the activated photosensitizer, --

Column 2,
Lines 24-27, please replace "Besides the properties discussed previously, the preferential tumor localization, stability, singlet oxygen producing efficiency, stability, low toxicity and solubility in appropriate injectable solvents are other important factors to be considered in developing an effective PDT agent." with -- Besides the properties discussed previously, the preferential tumor localization, stability, singlet oxygen producing efficiency, low toxicity and solubility in appropriate injectable solvents are other important factors to be considered in developing an effective PDT agent. --

Column 6,
Line 36, please replace "ethereal layer" with -- ether layer --

Signed and Sealed this

Fifth Day of October, 2004

JON W. DUDAS
*Director of the United States Patent and Trademark Office*